US009440998B2

(12) United States Patent
Moser et al.

(10) Patent No.: US 9,440,998 B2
(45) Date of Patent: Sep. 13, 2016

(54) PROCESS FOR PREPARING UREA-CONTAINING MERCAPTOSILANES

(71) Applicant: Evonik Industries AG, Essen (DE)

(72) Inventors: Ralph Moser, Freiburg i. Br. (DE); Caren Röben, Köln (DE); Stefanie Mayer, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/711,468

(22) Filed: May 13, 2015

(65) Prior Publication Data

US 2015/0329572 A1    Nov. 19, 2015

(30) Foreign Application Priority Data

May 15, 2014  (DE) .................. 10 2014 209 221

(51) Int. Cl.
C07F 7/10       (2006.01)
C07F 7/18       (2006.01)

(52) U.S. Cl.
CPC .................... C07F 7/1836 (2013.01)

(58) Field of Classification Search
CPC .................................................. C07F 7/1836
USPC ........................................................ 556/421
See application file for complete search history.

(56) References Cited

U.S. PATENT DOCUMENTS

| 2,509,483 | A | 5/1950 | Crouch |
| 3,637,789 | A | 1/1972 | Legendre |
| 3,946,059 | A | 3/1976 | Janssen et al. |
| 6,375,789 | B1 | 4/2002 | Katz |
| 2003/0191270 | A1 | 10/2003 | Musa |
| 2009/0075096 | A1* | 3/2009 | Butikofer .............. C07F 7/1836 428/447 |

FOREIGN PATENT DOCUMENTS

| DE | 3424534 | 1/1986 |
| DE | 10351735 | 12/2004 |
| DE | 60018483 | 1/2006 |
| EP | 1156053 | 11/2001 |
| EP | 1700861 | 9/2006 |
| EP | 2570419 | 3/2013 |
| JP | S59144792 | 8/1984 |
| JP | 2002201312 | 7/2002 |
| JP | 2002311574 | 10/2002 |
| JP | 2008279736 | 11/2008 |
| WO | 99/55754 | 11/1999 |
| WO | 2013/087698 | 6/2013 |

OTHER PUBLICATIONS

Wang et al., Database Accession No. 2014:1102076 (2014).
German Search Report for Application No. 15165590.9 dated Oct. 23, 2015 (9 pages).
Besson et al., "Soft route for monodisperse gold nanoparticles confined within SH– functionalized walls of mesoporous silica," J. Mat. Chem., 2009, 19, pp. 4746-4752.
German Search report for Application No. 102014209215.9 dated Jul. 31, 2014 (6 pages).
German Search report for Application No. 102014209221.3 dated Jul. 31, 2014 (5 pages).
German Search Report for Application No. 102014209226.4 dated Aug. 5, 2014 (6 pages).
German Search Report for Application No. 102014209239.6 dated Oct. 8, 2014 (6 pages).
Harpp et al., "Organic Sulfur Chemistry. X. Selective Desulfurization of Disulfides. Scope and Mechanism," Organic Sulfur Chemistry, 1970, pp. 2437-2443.
Wang et al, "Fabrication of Single-Hole Glutathione-Responsive Degradable Hollow Silica Nanoparticles for Drug Delivery," Applied Materials and Interfaces, American Chemical Society, 2014, 6, pp. 12600-12608.
United States Patent Office Notice of Allowance for U.S. Appl. No. 14/711,478 dated Jul. 17, 2015 (8 pages).
German Search Report for Application No. 102014209233.7 dated Oct. 13, 2014 (6 pages).
European Patent Office Search Report for Application No. 15165635.2 dated Sep. 17, 2015 (3 pages).
European Patent Office Search Report for Application No. 15161560.6 dated Oct. 7, 2015 (6 pages).
European Patent Office Search Report for Application No. 15161573.9 dated Oct. 2, 2015 (7 pages).
European Patent Office Search Report for Application No. 15161605.9 dated Oct. 6, 2015 (8 pages).
Xu et al., "A new strategy to prepare glutathione responsive silica nanoparticles," RSC Advances, 2013, 3, p. 17700.

(Continued)

*Primary Examiner* — Porfirio Nazario Gonzalez
*Assistant Examiner* — Kofi Adzamli
(74) *Attorney, Agent, or Firm* — Michael Best & Friedrich LLP

(57) ABSTRACT

The invention relates to a process for preparing urea-containing mercaptosilanes of the general formula I

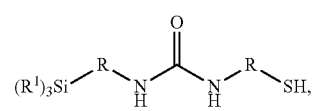

wherein a chlorosilane of the general formula II

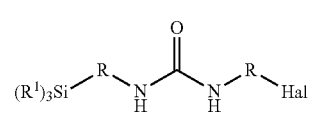

is reacted with NaSH in C2-C8 alcohol.

11 Claims, No Drawings

(56) References Cited

OTHER PUBLICATIONS

Gudima, N.V. et al., "Sorption of gold and palladium on silica gel modified by N-(4-mercaptophenyl)-N'-propylurea groups," Ukrainskii Khimicheskii Zhurnal (Russian Edition), 2010, 76, pp. 114-118.

Mane et al., "An efficient and greener protocol towards synthesis of unsymetrical N,N'-biphenyl urea," Arabian Journal of Chemistry, 2011, 6, pp. 423-427.

United States Patent Office Notice of Allowance for U.S. Appl. No. 14/711,478 dated Sep. 25, 2015 (5 pages).

United States Patent Office Notice of Allowance for U.S. Appl. No. 14/711,486 dated Mar. 11, 2016 (10 pages).

United States Patent Office Notice of Allowance for U.S. Appl. No. 14/711,463 dated May 20, 2016 (11 pages).

United States Patent Office Action for U.S. Appl. No. 14/711,473 dated May 11, 2016 (8 pages).

* cited by examiner

PROCESS FOR PREPARING UREA-CONTAINING MERCAPTOSILANES

CROSS-REFERENCE TO RELATED APPLICATIONS

This patent application claims the benefit of priority to German Application No. 102014209221.3, filed on May 15, 2014, the disclosure of which is incorporated by reference herein in its entirety, and priority to which is hereby claimed.

The invention relates to a process for preparing urea-containing mercaptosilanes.

CAS 1082204-82-7, 1268617-33-9 and 104261-54-3 disclose compounds of the formula

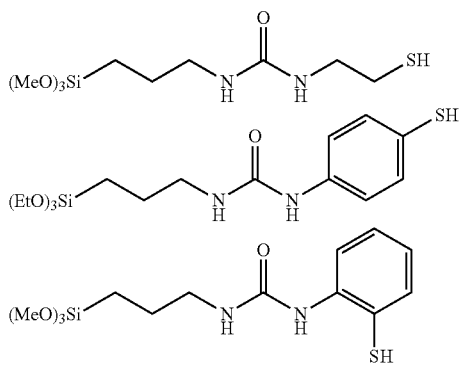

In addition, JP 2008279736 A discloses urea-containing silanes for coatings.

DE 3424534 A1 discloses N,N'- and N,N',N'-substituted urea-containing silanes of the formula

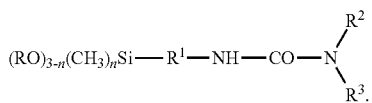

The preparation is effected by reacting an amino compound, a halosilane and alkali metal cyanate in an aprotic polar organic solvent, for example DMF or DMSO.

In addition, JP 2002311574 discloses powder coatings comprising silanes of the formula $R^1$—S—$R^2$—NH—C(O)—NH—$R^3$—Si($R^4$)$_m$ (O$R^5$)$_{3-m}$.

WO 9955754 A1 discloses photosensitive resin compositions comprising alkoxysilanes of the formula

[($R^1$O)$_{3-a}$($R^2$)$_a$Si—$R^3$-A-C(O)—B]$_m$—X.

A disadvantage of the known preparation process is the use of organic solvents, for example DMF or DMSO, and starting compounds, for example KOCN or NaOCN, that are hazardous to health. A further disadvantage is the complex workup.

It is an object of the present invention to provide a process which, compared to the processes from the prior art, works without organic solvents and starting compounds that are hazardous to health and has a simple workup.

The invention provides a process for preparing urea-containing mercaptosilanes of the general formula I

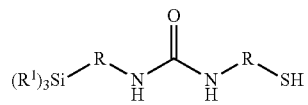

where $R^1$ are the same or different and are C1-C10 alkoxy groups, preferably methoxy or ethoxy group, C2-C10 cyclic dialkoxy group, phenoxy group, C4-C10 cycloalkoxy groups, C6-C20 aryl groups, preferably phenyl, C1-C10 alkyl group, preferably methyl or ethyl, C2-C20 alkenyl group, C7-C20 aralkyl group or halogen, preferably Cl, and R are the same or different and are a branched or unbranched, saturated or unsaturated, aliphatic, aromatic or mixed aliphatic/aromatic divalent $C_1$-$C_{30}$, preferably $C_1$-$C_{20}$, more preferably $C_1$-$C_{10}$, even more preferably $C_1$-$C_7$, especially preferably C2 and C3, hydrocarbon group optionally substituted by F—, Cl—, Br—, I—, —CN or HS—, which is characterized in that a halosilane of the general formula II

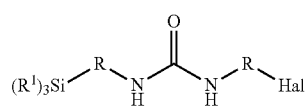

is reacted with NaSH, where R and $R^1$ are each as defined above and Hal is F, Cl, Br or I, preferably Cl, in C2-C8 alcohol, preferably ethanol.

Urea-containing mercaptosilanes may be mixtures of urea-containing mercaptosilanes of the general formula I.

The process product may comprise oligomers which form through hydrolysis and condensation of the alkoxysilane functions of the urea-containing mercaptosilanes of the general formula I.

R may preferably be

—$CH_2$—, —$CH_2CH_2$—, —$CH_2CH_2CH_2$—, —$CH_2CH_2CH_2CH_2$—, —CH($CH_3$)—, —$CH_2$CH($CH_3$)—, —CH($CH_3$)$CH_2$—, —C($CH_3$)$_2$—, —CH—($C_2H_5$)—, —$CH_2CH_2$CH($CH_3$)—, —CH($CH_3$)$CH_2CH_2$—,

—$CH_2$CH($CH_3$)$CH_2$—, —$CH_2CH_2CH_2CH_2CH_2$—, —$CH_2CH_2CH_2CH_2CH_2CH_2$—,

—$CH_2CH_2CH_2CH_2CH_2CH_2CH_2$—, —$CH_2CH_2CH_2CH_2CH_2CH_2CH_2CH_2$—,

—$CH_2CH_2CH_2CH_2CH_2CH_2CH_2CH_2CH_2$—, —$CH_2CH_2CH_2CH_2CH_2CH_2CH_2CH_2CH_2CH_2$—, —$CH_2CH_2CH_2CH_2CH_2CH_2CH_2CH_2CH_2CH_2CH_2$—,

—$CH_2CH_2CH_2CH_2CH_2CH_2CH_2CH_2CH_2CH_2CH_2CH_2$—,

—$CH_2CH_2CH_2CH_2CH_2CH_2CH_2CH_2CH_2CH_2CH_2CH_2CH_2$—,

—$CH_2CH_2CH_2CH_2CH_2CH_2CH_2CH_2CH_2CH_2CH_2CH_2CH_2CH_2$—,

—CH₂CH₂CH₂CH₂CH₂CH₂CH₂CH₂CH₂
CH₂CH₂CH₂CH₂CH₂CH₂CH₂CH₂CH₂—
or

[chemical structure: -CH₂-C₆H₄-CH₂CH₂- ] or

[chemical structure: -CH₂CH₂-C₆H₄-CH₂CH₂- ]

Urea-containing mercaptosilanes of the general formula I may preferably be:
(EtO)₃Si—CH₂—NH—CO—NH—CH₂—SH,
(EtO)₃Si—CH₂CH₂—NH—CO—NH—CH₂—SH,
(EtO)₃Si—CH₂—NH—CO—NH—CH₂CH₂—SH,
(EtO)₃Si—CH₂CH₂—NH—CO—NH—CH₂CH₂—SH,
(EtO)₃Si—CH₂CH₂CH₂—NH—CO—NH—CH₂—SH,
(EtO)₃Si—CH₂CH₂CH₂—NH—CO—NH—CH₂CH₂—SH,
(EtO)₃Si—CH₂—NH—CO—NH—CH₂CH₂CH₂—SH,
(EtO)₃Si—CH₂CH₂—NH—CO—NH—CH₂CH₂CH₂—SH,
(EtO)₃Si—CH₂CH₂CH₂—NH—CO—NH—CH₂CH₂CH₂—SH,
(MeO)₃Si—CH₂—NH—CO—NH—CH₂—SH,
(MeO)₃Si—CH₂CH₂—NH—CO—NH—CH₂—SH,
(MeO)₃Si—CH₂—NH—CO—NH—CH₂CH₂—SH,
(MeO)₃Si—CH₂CH₂—NH—CO—NH—CH₂CH₂—SH,
(MeO)₃Si—CH₂CH₂CH₂—NH—CO—NH—CH₂—SH,
(MeO)₃Si—CH₂CH₂CH₂—NH—CO—NH—CH₂CH₂—SH,
(MeO)₃Si—CH₂—NH—CO—NH—CH₂CH₂CH₂—SH,
(MeO)₃Si—CH₂CH₂—NH—CO—NH—CH₂CH₂CH₂—SH oder
(MeO)₃Si—CH₂CH₂CH₂—NH—CO—NH—CH₂CH₂CH₂—SH.

An especially preferred compound is of the formula (EtO)₃Si—CH₂CH₂CH₂—NH—CO—NH—CH₂CH₂—SH Halosilanes of the general formula II may preferably be:
(EtO)₃Si—CH₂—NH—CO—NH—CH₂—Cl,
(EtO)₃Si—CH₂CH₂—NH—CO—NH—CH₂—Cl,
(EtO)₃Si—CH₂—NH—CO—NH—CH₂CH₂—Cl,
(EtO)₃Si—CH₂CH₂—NH—CO—NH—CH₂CH₂—Cl,
(EtO)₃Si—CH₂CH₂CH₂—NH—CO—NH—CH₂—Cl,
(EtO)₃Si—CH₂CH₂CH₂—NH—CO—NH—CH₂CH₂—Cl
(EtO)₃Si—CH₂—NH—CO—NH—CH₂CH₂CH₂—Cl,
(EtO)₃Si—CH₂CH₂—NH—CO—NH—CH₂CH₂CH₂—Cl,
(EtO)₃Si—CH₂CH₂CH₂—NH—CO—NH—CH₂CH₂CH₂—Cl,
(MeO)₃Si—CH₂—NH—CO—NH—CH₂—Cl,
(MeO)₃Si—CH₂CH₂—NH—CO—NH—CH₂—Cl,
(MeO)₃Si—CH₂—NH—CO—NH—CH₂CH₂—Cl,
(MeO)₃Si—CH₂CH₂—NH—CO—NH—CH₂CH₂—Cl,
(MeO)₃Si—CH₂CH₂CH₂—NH—CO—NH—CH₂—Cl,
(MeO)₃Si—CH₂CH₂CH₂—NH—CO—NH—CH₂CH₂—Cl,
(MeO)₃Si—CH₂—NH—CO—NH—CH₂CH₂CH₂—Cl,
(MeO)₃Si—CH₂CH₂—NH—CO—NH—CH₂CH₂CH₂—Cl,
(MeO)₃Si—CH₂CH₂CH₂—NH—CO—NH—CH₂CH₂CH₂—Cl,
(EtO)₃Si—CH₂—NH—CO—NH—CH₂—Br,
(EtO)₃Si—CH₂CH₂—NH—CO—NH—CH₂—Br,
(EtO)₃Si—CH₂—NH—CO—NH—CH₂CH₂—Br,
(EtO)₃Si—CH₂CH₂—NH—CO—NH—CH₂CH₂—Br,
(EtO)₃Si—CH₂CH₂CH₂—NH—CO—NH—CH₂—Br,
(MeO)₃Si—CH₂CH₂CH₂—NH—CO—NH—CH₂CH₂CH₂—Br,
(EtO)₃Si—CH₂—NH—CO—NH—CH₂CH₂CH₂—Br,
(EtO)₃Si—CH₂CH₂—NH—CO—NH—CH₂CH₂CH₂—Br,
(EtO)₃Si—CH₂CH₂CH₂—NH—CO—NH—CH₂CH₂CH₂—Br,
(MeO)₃Si—CH₂—NH—CO—NH—CH₂—Br,
(MeO)₃Si—CH₂CH₂—NH—CO—NH—CH₂—Br,
(MeO)₃Si—CH₂—NH—CO—NH—CH₂CH₂—Br,
(MeO)₃Si—CH₂CH₂—NH—CO—NH—CH₂CH₂—Br,
(MeO)₃Si—CH₂CH₂CH₂—NH—CO—NH—CH₂—Br,
(MeO)₃Si—CH₂CH₂CH₂—NH—CO—NH—CH₂CH₂—Br,
(MeO)₃Si—CH₂—NH—CO—NH—CH₂CH₂CH₂—Br,
(MeO)₃Si—CH₂CH₂—NH—CO—NH—CH₂CH₂CH₂—Br or
(MeO)₃Si—CH₂CH₂CH₂—NH—CO—NH—CH₂CH₂CH₂—Br.

The urea-containing mercaptosilane of the general formula I obtainable by the process according to the invention can be obtained in a yield of greater than 50%, preferably greater than 60%, more preferably greater than 70%, very preferably greater than 80%.

The soluble fraction in the product obtained by the process according to the invention in DMSO-d⁶ or CDCl₃ is determined by adding an internal standard, for example triphenylphosphine oxide (TPPO), in DMSO-d6 or in CDCl₃, and a ¹H NMR method known to those skilled in the art.

It is possible to use further solvents for the reaction, for example inorganic or organic solvents.

The reaction can be conducted without additional organic solvent.

In relation to the halosilanes of the general formula II used, the amount of water may be less than 10% by weight, preferably less than 5% by weight, more preferably less than 2% by weight and very preferably less than 1% by weight.

The reaction can be conducted with exclusion of air.

The reaction may be carried out under an inert gas atmosphere, for example under argon or nitrogen, preferably under nitrogen.

The process of the invention can be carried out at atmospheric pressure, elevated pressure or reduced pressure. Preferably, the process according to the invention can be conducted at standard pressure.

Elevated pressure may be a pressure from 1.1 bar to 100 bar, preferably of 1.5 bar to 50 bar, more preferably of 2 bar to 20 bar and very preferably of 2 to 10 bar.

Reduced pressure may be a pressure of 1 mbar to 1000 mbar, preferably 1 mbar to 500 mbar, more preferably 1 mbar to 250 mbar, very preferably 5 mbar to 100 mbar.

The process according to the invention can be conducted between 0° C. and +150° C., preferably between +20° C. and +130° C., more preferably between +50° C. and +100° C.

In the process according to the invention, halosilane of the general formula II can be metered into NaSH.

In the process according to the invention, NaSH can be metered into halosilane of the general formula II.

The halosilane of the general formula II, prior to the reaction with NaSH, can be prepared from the hydrochloride salt of an amine of the general formula III

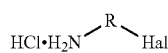  (III)

and isocyanatosilane of the general formula IV

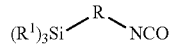  (IV)

by addition of a base, preferably NaOEt, where Hal, R and $R^1$ are each as defined above.

The base can be added until a pH between 7 and 14 is established.

In the process according to the invention, the hydrochloride salts of the amines of the general formula III can be used relative to isocyanatosilanes of the general formula IV in a molar ratio of 1:0.80 to 1:1.20, preferably 1:0.85 to 1:1.15, more preferably in a ratio of 1:0.90 to 1:1.10.

Hydrochloride salts of the amines of the general formula III may preferably be:
Hcl.$H_2$N—$CH_2$—Cl,
Hcl.$H_2$N—$CH_2$—$CH_2$—Cl,
Hcl.$H_2$N—$CH_2$—$CH_2$—$CH_2$—Cl,
Hcl.$H_2$N—$CH_2$—Br,
Hcl.$H_2$N—$CH_2$—$CH_2$—Br or
Hcl.$H_2$N—$CH_2$—$CH_2$—$CH_2$—Br.

Isocyanatosilanes of the general formula IV may preferably be:
$(EtO)_3$Si—$CH_2$—NCO,
$(EtO)_3$Si—$CH_2$—$CH_2$—NCO,
$(EtO)_3$Si—$CH_2$—$CH_2$—$CH_2$—NCO,
$(MeO)_3$Si—$CH_2$—NCO,
$(MeO)_3$Si—$CH_2$—$CH_2$—NCO or
$(MeO)_3$Si—$CH_2$—$CH_2$—$CH_2$—NCO.

The halosilane of the general formula II, prior to the reaction with NaSH, can be prepared from the isocyanate-halogen compound of the general formula V

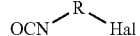  (V)

and aminosilane of the general formula VI

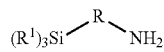  (VI)

where Hal, R and $R^1$ are each as defined above.

The reaction can be conducted in a solvent, preferably C2-C8 alcohol, more preferably ethanol.

In the process according to the invention, the isocyanate-halogen compounds of the general formula V can be used relative to aminosilanes of the general formula VI in a molar ratio of 1:0.80 to 1:1.20, preferably 1:0.85 to 1:1.15, more preferably in a ratio of 1:0.90 to 1:1.10.

Isocyanate-halogen compounds of the general formula V may preferably be:
OCN—$CH_2$—Cl,
OCN—$CH_2$—$CH_2$—Cl,
OCN—$CH_2$—$CH_2$—$CH_2$—Cl,
OCN—$CH_2$—Br,
OCN—$CH_2$—$CH_2$—Br or
OCN—$CH_2$—$CH_2$—$CH_2$—Br.

Aminosilane compounds of the general formula VI may preferably be:
$(EtO)_3$Si—$CH_2$—$NH_2$,
$(EtO)_3$Si—$CH_2$—$CH_2$—$NH_2$,
$(EtO)_3$Si—$CH_2$—$CH_2$—$CH_2$—$NH_2$,
$(MeO)_3$Si—$CH_2$—$NH_2$,
$(MeO)_3$Si—$CH_2$—$CH_2$—$NH_2$ or
$(MeO)_3$Si—$CH_2$—$CH_2$—$CH_2$—$NH_2$.

The product prepared by the process according to the invention may have a residual content of halosilane of the general formula II of less than 25 mol %, preferably less than 10 mol %, more preferably less than 5 mol %, very preferably less than 3 mol %.

The relative molar percentages of the halosilanes of the general formula II in the product prepared by the process according to the invention are determined in the $^1$H NMR by integration of the hydrogen atoms in the —$CH_2C\underline{H}_2$—Cl group of the halosilanes of the general formula II against the hydrogen atoms in the Si—$C\underline{H}_2$— group of the urea-containing mercaptosilanes of the general formula I.

For the substance of the formula II $(EtO)_3$Si—$CH_2CH_2CH_2$—NH—CO—NH—$CH_2CH_2$—Cl, for example, the integral of the hydrogen atoms of the —$CH_2C\underline{H}_2$—Cl group (δ=3.17 ppm) is used for the determination of the relative contents.

The product prepared by the process according to the invention may have a residual content of hydrochloride salt of an amine of the general formula III of less than 10 mol %, preferably less than 5 mol %, more preferably less than 1 mol %, very preferably less than 0.1 mol %.

The relative molar percentages of the hydrochloride salts of an amine of the general formula III in the product prepared by the process according to the invention are determined in the $^{13}$C NMR by integration of the carbon atoms in the —$\underline{C}H_2$—$NH_2$.HCl group of the hydrochloride salts of an amine of the general formula III against the carbon atoms in the Si—$\underline{C}H_2$— group of the urea-containing mercaptosilanes of the general formula I.

For the substance of the formula III HCl.$H_2$N—$CH_2$—$CH_2$—Cl, for example, the integral of the carbon atoms of the HCl.$H_2$N—$\underline{C}H_2$—$CH_2$—Cl group (δ=41.25 ppm) or of the HCl.$H_2$N—$CH_2$—$\underline{C}H_2$—Cl group (δ=40.79 ppm) is used for the determination of the relative contents.

The product prepared by the process according to the invention may have a residual content of isocyanatosilane of the general formula IV of less than 10 mol %, preferably less than 5 mol %, more preferably less than 1 mol %, very preferably less than 0.1 mol %.

The relative molar percentages of the isocyanatosilanes of the general formula IV in the product within a range of >1 mol %, prepared by the process according to the invention, are determined in the $^{13}$C NMR by integration of the carbon atoms in the —N$\underline{C}$O group of the isocyanatosilanes of the general formula IV against the carbon atoms in the Si—$\underline{C}H_2$— group of the urea-containing mercaptosilanes of the general formula I.

For the substance of the formula IV $(EtO)_3$Si—$CH_2$—$CH_2$—$CH_2$—NCO, for example, the integral of the carbon atoms of the —N$\underline{\text{C}}$O group (δ=122.22 ppm) is used for the determination of the relative contents within a range of >1 mol %.

The relative molar percentages of the isocyanatosilanes of the general formula IV in the product within a range of <1 mol %, prepared by the process according to the invention, are determined by quantitative FT-IR spectroscopy known to those skilled in the art. The method is calibrated by using calibration solutions of suitable concentration (for example in $C_2Cl_4$). For the measurement, about 1 g of sample is weighed into a 25 ml rollneck bottle, and 25 g of $C_2Cl_4$ are added. The sample is agitated on an agitator for 1-2 hours. Thereafter, the lower liquid phase is metered cautiously into a 20 mm IR cuvette and analysed by FT-IR spectroscopy (4000-1200 $cm^{-1}$, resolution 2 $cm^{-1}$). Under the same conditions, a spectrum of the solvent is recorded for subtraction.

For the substance of the formula IV $(EtO)_3Si$—$CH_2$—$CH_2$—$CH_2$—NCO, for example, the wavelength of the valence vibration of the —NCO group at 2270 $cm^{-1}$ is used for the determination of the relative contents within a range of <1 mol %.

The product prepared by the process according to the invention may have a residual content of isocyanate-halogen compounds of the general formula V of less than 25 mol %, preferably less than 10 mol %, more preferably less than 5 mol %, very preferably less than 3 mol %.

The relative molar percentages of the isocyanate-halogen compounds of the general formula V in the product prepared by the process according to the invention are determined in the $^{13}$C NMR by integration of the carbon atoms in the O$\underline{\text{C}}$N—$CH_2$— group of the isocyanate-halogen compounds of the general formula V against the carbon atoms in the Si—$\underline{\text{CH}}_2$— group of the urea-containing mercaptosilanes of the general formula I.

For the substance of the formula V OCN—$CH_2$—$CH_2$—Cl, for example, the integral of the carbon atoms of the O$\underline{\text{C}}$N—$CH_2$— group (δ=124.33 ppm) is used for the determination of the relative contents.

The product prepared by the process according to the invention may have a residual content of aminosilanes of the general formula VI of less than 10 mol %, preferably less than 5 mol %, more preferably less than 1 mol %, very preferably less than 0.1 mol %.

The relative molar percentages of the aminosilanes of the general formula VI in the product prepared by the process according to the invention are determined in the $^{13}$C NMR by integration of the carbon atoms in the —$\underline{\text{CH}}_2$—$NH_2$ group of the aminosilanes of the general formula VI against the carbon atoms in the Si—$\underline{\text{CH}}_2$— group of the urea-containing mercaptosilanes of the general formula I.

For the substance of the formula VI $(EtO)_3Si$—$CH_2$—$CH_2$—$CH_2$—$NH_2$, for example, the integral of the carbon atoms of the —$\underline{\text{CH}}_2$—$NH_2$ group (δ=45.15 ppm) is used for the determination of the relative contents.

The reaction mixture can be filtered and the alcohol can then be distilled off and the product can be dried. The drying can be effected at 20° C.-100° C., optionally at a reduced pressure of 1 mbar-500 mbar.

In one embodiment, the process for preparing urea-containing mercaptosilanes of the general formula I

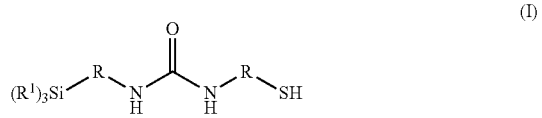

(I)

may be characterized in that a hydrochloride salt of an amine of the general formula III

(III)

and isocyanatosilane of the general formula IV

(IV)

is converted by adding a base in C2-C8 alcohol, preferably ethanol, and then the NaSH is added, the reaction mixture is filtered, the alcohol is distilled off and the product is dried, where Hal, R and $R^1$ are each as defined above.

In a second embodiment, the process for preparing urea-containing mercaptosilanes of the general formula I

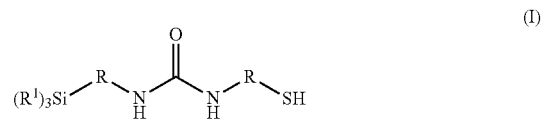

(I)

may be characterized in that an isocyanate-halogen compound of the general formula V

(V)

and aminosilane of the general formula VI

(VI)

is converted in C2-C8 alcohol, preferably ethanol, and then the NaSH is added, the reaction mixture is filtered, the alcohol is distilled off and the product is dried, where Hal, R and $R^1$ are each as defined above.

The urea-containing mercaptosilanes of the general formula I can be used as adhesion promoters between inorganic materials, for example:

glass beads, glass shards, glass surfaces, glass fibres, or oxidic fillers, preferably silicas such as precipitated silicas and fumed silicas, and organic polymers, for example thermosets, thermoplastics or elastomers, or as crosslinking agents and surface modifiers for oxidic surfaces.

The urea-containing mercaptosilanes of the general formula I may be used as coupling reagents in filled rubber mixtures, examples being tyre treads, industrial rubber articles or footwear soles.

The advantage of the process according to the invention is that the preparation of urea-containing mercaptosilanes of the general formula I is possible without organic solvents and starting compounds that are hazardous to health.

A further advantage of the process according to the invention is that a complex purification of the products obtained can be dispensed with.

EXAMPLE 1

Preparation of (EtO)₃Si—CH₂CH₂CH₂—NH—CO—NH—CH₂CH₂—SH from (EtO)₃Si—CH₂CH₂CH₂—NH—CO—NH—CH₂CH₂—Cl and NaSH To a solution of NaSH in ethanol [prepared by introducing H₂S (15.21 g, 0.45 mol, 1.07 eq) into a sodium ethoxide solution (prepared from Na (10.55 g, 0.46 mol, 1.10 eq) in EtOH (300 mL))] is added, by metered addition at 52° C., (EtO)₃Si—CH₂CH₂CH₂—NH—CO—NH—CH₂CH₂—Cl (138.90 g, 0.42 mol, 1.00 eq) in ethanol (300 ml), and the mixture is heated to 78° C. After a reaction time of 5 h, the mixture is cooled to room temperature and the suspension is filtered. The filtrate is freed of the solvent on a rotary evaporator and dried under reduced pressure. The (EtO)₃Si—CH₂CH₂CH₂—NH—CO—NH—CH₂CH₂—SH product (134.96 g, 97.9% of theory) is obtained as a white solid.

¹H NMR ($\delta_{ppm}$, 500 MHz, CDCl₃): 0.64 (2H, t), 1.23 (9H, t), 1.36 (1H, br), 1.61 (2H, m), 2.67 (2H, t), 3.17 (2H, m), 3.37 (2H, m), 3.81 (6H, q), 4.74 (1H, br), 4.94 (1H, br);

¹³C NMR ($\delta_{ppm}$, 125 MHz, CDCl₃): 7.8 (1C), 18.3 (3C), 23.8 (1C), 25.6 (1C), 43.0 (1C), 43.5 (1C), 58.4 (3C), 158.9 (1C).

EXAMPLE 2

Preparation of (EtO)₃Si—CH₂CH₂CH₂—NH—CO—NH—CH₂CH₂—SH from (EtO)₃Si—CH₂CH₂CH₂—NH₂, OCN—CH₂CH₂—Cl and NaSH 3-Aminopropyltriethoxysilane (154.95 g, 0.70 mol, 1.00 eq) is initially charged in ethanol (3.0 l) in a 4 l three-neck flask with precision glass stirrer, internal thermometer, dropping funnel and reflux condenser, and cooled to −78° C. 2-Chloroethyl isocyanate (73.86 g, 0.70 mol, 1.00 eq) is added dropwise at −78 to −69° C. within 2.5 h and then the mixture is heated to 50° C. A solution of NaSH [analogous preparation to Example 1 from 21% NaOEt solution in EtOH (244.98 g, 0.76 mol, 1.09 eq) and H₂S (25.06 g, 0.74 mol, 1.05 eq)] is added within 50 min and the mixture is heated to 78° C. After a reaction time of 5 h, the mixture is cooled to room temperature and the suspension is filtered. The filtrate is freed of the solvent on a rotary evaporator and dried under reduced pressure. The (EtO)₃Si—CH₂CH₂CH₂—NH—CO—NH—CH₂CH₂—SH product (208.07 g, 90.8% of theory) is obtained as a white solid.

¹H NMR ($\delta_{ppm}$, 500 MHz, CDCl₃): 0.64 (2H, t), 1.22 (9H, t), 1.36 (1H, br), 1.61 (2H, m), 2.67 (2H, t), 3.16 (2H, m), 3.37 (2H, m), 3.81 (6H, q), 4.65 (1H, br), 4.84 (1H, br).

EXAMPLE 3

Preparation of (EtO)₃Si—CH₂CH₂CH₂—NH—CO—NH—CH₂CH₂—SH from (EtO)₃Si—CH₂CH₂CH₂—NCO, HCl·H₂N—CH₂CH₂—Cl and NaSH 2-Chloroethylamine hydrochloride (73.86 g, 0.70 mol, 1.00 eq) is initially charged in ethanol (3.0 l) in a 4 l three-neck flask with precision glass stirrer, internal thermometer, dropping funnel and reflux condenser, and cooled to −78° C., and sodium ethoxide (226.83 g, 0.70 mol, 1.00 eq, 21% in ethanol) is added. 3-Isocyanatopropyl(triethoxysilane) (173.15 g, 0.70 mol, 1.00 eq) is then added dropwise at −78 to −70° C. within 3 h and then the mixture is heated to 50° C. A solution of NaSH [analogous preparation to Example 1 from 21% NaOEt solution in EtOH (244.98 g, 0.76 mol, 1.09 eq) and H₂S (25.06 g, 0.74 mol, 1.05 eq)] is added within 50 min and the mixture is heated to 78° C. After a reaction time of 5 h, the mixture is cooled to room temperature and the suspension is filtered. The filtrate is freed of the solvent on a rotary evaporator and dried under reduced pressure. The (EtO)₃Si—CH₂CH₂CH₂—NH—CO—NH—CH₂CH₂—SH product (220.34 g, 96.9% of theory) is obtained as a pale yellowish oil.

What is claimed is:
1. A process for preparing a urea-containing mercaptosilane of formula I

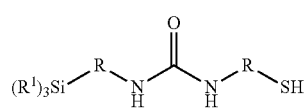

where each R¹ is independently selected from the group consisting of a C1-C10 alkoxy group, a C2-C10 cyclic dialkoxy group, a phenoxy group, a C4-C10 cycloalkoxy group, a C6-C20 aryl group, a C1-C10 alkyl group, a C2-C20 alkenyl group, a C7-C20 aralkyl group or a halogen, and each R is independently a branched or unbranched, saturated or unsaturated, aliphatic, aromatic or mixed aliphatic/aromatic divalent C1-C30 hydrocarbon group, the process comprising reacting a halosilane of formula II

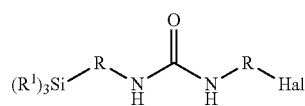

where Hal is F, Cl, Br or I
with NaSH in a C2-C8 alcohol.
2. The process of claim 1, wherein the alcohol is ethanol.
3. The process of claim 1, wherein the urea-containing mercaptosilane is
(EtO)₃Si—CH₂—NH—CO—NH—CH₂—SH,
(EtO)₃Si—CH₂CH₂—NH—CO—NH—CH₂—SH,
(EtO)3Si—CH2-NH—CO—NH—CH2CH2-SH,
(EtO)3Si—CH2CH2-NH—CO—NH—CH2CH2-SH,
(EtO)3Si—CH2CH2CH2-NH—CO—NH—CH2-SH,
(EtO)3Si—CH2CH2CH2-NH—CO—NH—CH2CH2-SH,
(EtO)3Si—CH2-NH—CO—NH—CH2CH2CH2-SH,
(EtO)3Si—CH2CH2-NH—CO—NH—CH2CH2CH2-SH,
(EtO)3Si—CH2CH2CH2-NH—CO—NH—CH2CH2CH2-SH,
(MeO)3Si—CH2-NH—CO—NH—CH2-SH,
(MeO)3Si—CH2CH2-NH—CO—NH—CH2-SH,
(MeO)3Si—CH2-NH—CO—NH—CH2CH2-SH,
(MeO)3Si—CH2CH2-NH—CO—NH—CH2CH2-SH,
(MeO)3Si—CH2CH2CH2-NH—CO—NH—CH2-SH, (MeO)3Si—CH2CH2CH2-NH—CO—NH—CH2CH2-SH,
(MeO)3Si—CH2-NH—CO—NH—CH2CH2CH2-SH,
(MeO)3Si—CH2CH2-NH—CO—NH—CH2CH2CH2-SH or
(MeO)$_3$Si—CH$_2$CH$_2$CH$_2$—NH—CO—NH—CH$_2$CH$_2$CH$_2$—SH.

4. The process of claim 1, wherein the reaction is conducted without additional organic solvent.

5. The process of claim 1, wherein the reaction is conducted at a temperature between 0° C. and +150° C.

6. The process of claim 1, wherein the halosilane of formula II, prior to reaction with NaSH, is prepared from a hydrochloride salt of an amine of formula III

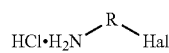

(III)

and an isocyanatosilane of formula IV

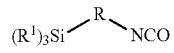

(IV)

by addition of a base.

7. The process of claim 6, wherein the base is NaOEt.

8. The process of claim 6, wherein the base is added until a pH between 7 and 14 is established.

9. The process of claim 1, wherein the halosilane of formula II, prior to reaction with NaSH, is prepared from an isocyanate-halogen compound of formula V

(V)

and an aminosilane of formula VI

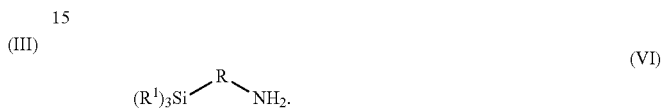

(VI)

10. The process of claim 1, further comprising filtering the reaction mixture and distilling off the alcohol.

11. The process of claim 10, further comprising drying a product formed from the reaction.

* * * * *